United States Patent
Sato et al.

(10) Patent No.: US 6,911,082 B2
(45) Date of Patent: Jun. 28, 2005

(54) METHOD OF MANUFACTURING A MULTI-LAYER SEMICONDUCTOR NANOPARTICLE, AND A MULTI-LAYER SEMICONDUCTOR NANOPARTICLE MANUFACTURED BY THE METHOD

(75) Inventors: Keiichi Sato, Tokyo (JP); Susumu Kuwabata, Osaka (JP)

(73) Assignee: Hitachi Software Engineering Co., LTD, Kanagawa (JP)

(*) Notice: Subject to any disclaimer, the term of this patent is extended or adjusted under 35 U.S.C. 154(b) by 52 days.

(21) Appl. No.: 10/348,002

(22) Filed: Jan. 22, 2003

(65) Prior Publication Data

US 2003/0162393 A1 Aug. 28, 2003

(30) Foreign Application Priority Data

Feb. 5, 2002 (JP) ....................... 2002-028022

(51) Int. Cl.[7] .................. C30B 25/12; C30B 25/14
(52) U.S. Cl. ................... 117/68; 2/3; 977/DIG. 1
(58) Field of Search .............. 117/2, 3, 68; 977/DIG. 1

(56) References Cited

U.S. PATENT DOCUMENTS 5,541,712 A 7/1996 Fujitaka et al.
6,403,056 B1 * 6/2002 Unger et al. ............... 424/9.51

FOREIGN PATENT DOCUMENTS

WO WO 99/26299 11/1998
WO 1 375 625 A1 6/2003

OTHER PUBLICATIONS

Dmitri V. Talapin et al., "Highly Luminescent Monodisperse CdSe and CdSe,ZnS Nanocrystals Synthesized in a Hexadecylamine–Trioctylphosphine Oxide–Trioctylphosphine Mixture", NANO Letters (2001), vol. 1., No. 4, pp. 207–211.

Shu–Hong Yu et al., "Benzene–Thermal Synthesis and Optical Properties and CdS Nanocrystalline", Nanostructured Materials, vol. 10, No. 8, (1998), pp. 1307–1316.

* cited by examiner

*Primary Examiner*—Felisa Hiteshew
(74) *Attorney, Agent, or Firm*—Reed Smith LLP; Stanley P. Fisher, Esq.; Juan Carlos A. Marquez, Esq.

(57) ABSTRACT

Multi-layered semiconductor nanoparticles having a very narrow grain-size distribution and exhibiting a spectrum having a narrow wavelength-width peak are prepared by a manufacturing method combining a monodisperse semiconductor nanoparticle manufacturing method and a multi-layer semiconductor nanoparticle preparation method. The nature of a solution of monodisperse semiconductor nanoparticles that is stabilized by a surface stabilizer is transformed between hydrophilic and lipophilic by substituting the surface stabilizer. The stabilized semiconductor nanoparticles are then shifted between an aqueous layer and an organic layer. The semiconductor nanoparticles are coated with multiple layers in the organic layer, and the organic layer is drawn off to recover the semiconductor nanoparticles therefrom.

10 Claims, 3 Drawing Sheets

METHOD OF MANUFACTURING A MULTI-LAYER SEMICONDUCTOR NANOPARTICLE, AND A MULTI-LAYER SEMICONDUCTOR NANOPARTICLE MANUFACTURED BY THE METHOD

BACKGROUND OF THE INVENTION

1. Technical Field

The present invention relates to a method of manufacturing a multi-layer semiconductor nanoparticle that emits fluorescence of a narrow wavelength width, and the multi-layer semiconductor nanoparticle manufactured by the method.

2. Background Art

Semiconductor nanoparticles of a grain size of 10 nm or less are located in the transition region between bulk semiconductor crystals and molecules. Their physicochemical properties are therefore different from both bulk semiconductor crystals and molecules. In this region, the energy gap of a semiconductor nanoparticle increases as its grain size decreases, due to the appearance of a quantum-size effect. In addition, the degeneracy of the energy band that is observed in bulk semiconductors is removed and the orbits are dispersed. As a result, a lower-end of the conduction band is shifted to the negative side and an upper-end of the valence band is shifted to the positive side.

Semiconductor nanoparticles can be easily prepared by dissolving equimolar amounts of precursors of Cd and X (X being S, Se or Te). This is also true for their manufacture using ZnS, ZnSe, HgS, HgSe, PbS, or PbSe, for example.

However, the semiconductor nanoparticles obtained by the above method exhibit a wide grain-size distribution and therefore cannot provide the full advantage of the properties of semiconductor nanoparticles. Attempts have been made to attain a monodisperse distribution by using chemical techniques to precisely separate the semiconductor nanoparticles having a wide grain-size distribution immediately after preparation into individual grain sizes and extract only those semiconductor nanoparticles of a particular grain size. The attempts that have been reported so far include an electrophoresis separation method that utilizes variation in the surface charge of a nanoparticle depending on the grain size, an exclusion chromatography that takes advantage of differences in retention time due to different grain sizes, a size-selective precipitation method utilizing differences in dispersibility into an organic solvent due to different grain sizes, and a size-selective photocorrosion.

Semiconductor nanoparticles obtained by these methods exhibit a spectrum with a relatively narrow wavelength-width peak, however, even in such a monodisperse state, the light-emission characteristics of the crystal are not quite satisfactory. This is presumably due to the presence of the energy level of a defect site on the particle surface in the forbidden band exhibited by the nanoparticle. Thus, by removing the energy band in the forbidden band, the light-emission characteristics of the semiconductor nanoparticle can be improved. Various methods have been attempted so far to remove the energy band in the forbidden band.

In one method, for example, the semiconductor nanoparticle surface is coated with an organic component such as tri-n-octyl phosphine (TOP) and tri-n-octyl phosphine oxide (TOPO). In another method, the semiconductor nanoparticle surface is coated with an inorganic component such as CdX and ZnX.

The semiconductor nanoparticle manufacturing method employing size-selective photocorrosion makes it possible to manufacture not only large quantities of semiconductor nanoparticles very easily but also manufacture semiconductor nanoparticles having a very narrow grain-size distribution. Further, by coating the surface of semiconductor nanoparticles with an inorganic component to remove the energy band in the forbidden band, multi-layer semiconductor nanoparticles that show a spectrum with a narrow wavelength-width peak can be prepared. However, it has been difficult to combine the former and the latter techniques into one process because of the difference in the stabilizer used.

SUMMARY OF THE INVENTION

In view of the above, there is a need for an effective manufacturing method that combines the method of manufacturing monodisperse semiconductor nanoparticles and the method of preparing multi-layer semiconductor nanoparticles. It is therefore an object of the invention to prepare multi-layer semiconductor nanoparticles that have a very narrow grain-size distribution and that exhibit a spectrum having a narrow wavelength-width peak.

In one aspect, the invention provides a method of manufacturing a multi-layer semiconductor nanoparticle, which comprises the steps of:

transforming the nature of a solution of monodisperse semiconductor nanoparticles stabilized by a surface stabilizer between hydrophilic and lipophilic by substituting the surface stabilizer;

transporting the stabilized semiconductor nanoparticles between an aqueous layer and an organic layer;

coating the semiconductor nanoparticles in the layer to which the stabilized semiconductor nanoparticles have been transported with multiple layers; and separating the layer to which the stabilized semiconductor nanoparticles have been transported to recover the semiconductor nanoparticles therefrom.

The monodisperse semiconductor nanoparticles are preferably obtained by a size-selective photocorrosion. Alternatively, they may be obtained by a reversed micelle method.

The surface stabilizer for providing the hydrophilicity is preferably hexametaphosphate, polyvinyl pyrrolidone, glycol dimethyl ether, or a thiol compound. The surface stabilizer for providing the lipophilicity is preferably tri-n-octyl phosphine or tri-n-octyl phosphine oxide.

More specifically, semiconductor nanoparticles whose nature has been transformed from hydrophilic to lipophilic may be reacted with zinc oxide, 1-tetradecane phosphoric acid (TDPA), tri-n-octyl phosphine oxide (TOPO), tri-n-octyl phosphine (TOP), and S (powder) in a high-temperature environment.

The material for the core and the material for the layers uniformly coated on the surface of the core may each be selected from ZnO, ZnS, ZnSe, ZnTe, CdO, CdS, CdSe, CdTe, HgS, HgSe, HgTe, InP, InAs, GaN, GaP, GaAs, $TiO_2$, $WO_3$, PbS and PbSe, for example.

For example, the material of the core may be CdS, and the material of the layers uniformly coated on the surface of the core may be ZnS.

When excited, the multi-layer semiconductor nanoparticle manufactured according to the method of the invention may emit fluorescence having a peak in a narrow wavelength-width region with a full width at half maximum (FWHM) of about 50 nm or less.

The nanoparticle preferably exhibits less than 10% rms deviation in the diameter of the core.

DESCRIPTION OF THE INVENTION

Figure 1:
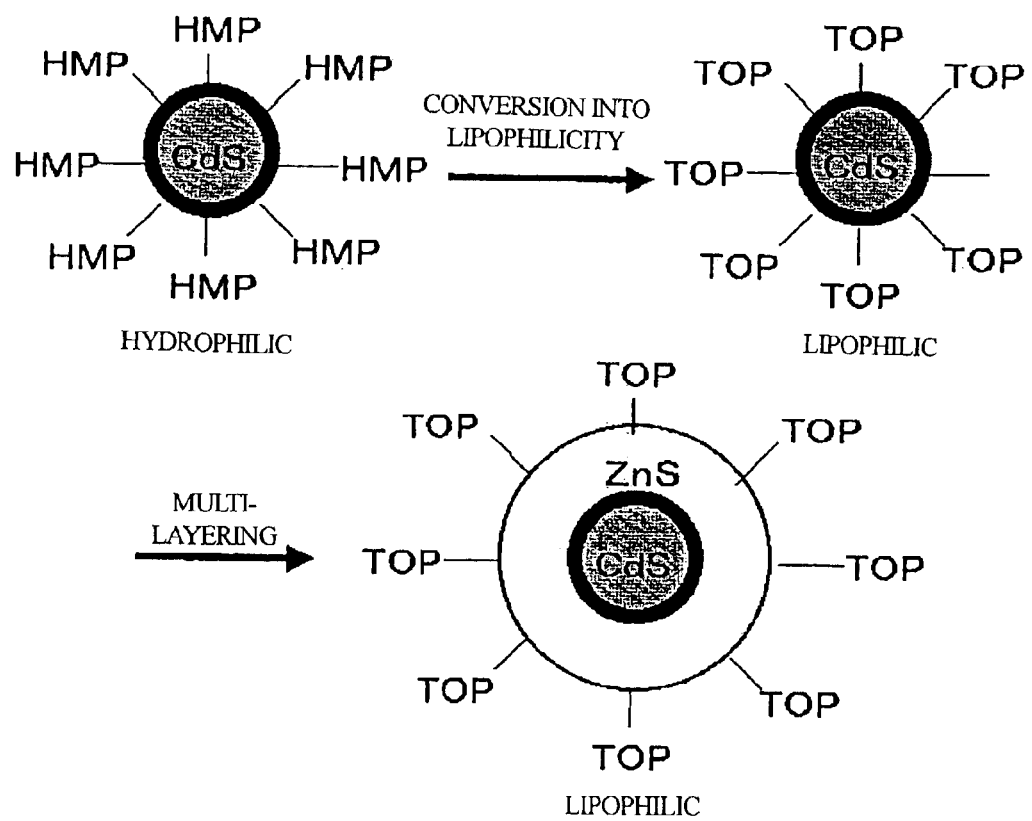
FIG. 1 shows the process of manufacturing a multi-layer semiconductor nanoparticle according to the invention.

FIG. 1 shows an example of the invention. A CdS semiconductor nanoparticle obtained by the size-selective photocorrosion, for example, is present in an aqueous solution, with the surface of the particle coated with a stabilizer, hexametaphosphate (HMP). When this aqueous solution is mixed with an organic solvent made up mainly of TOP and/or TOPO, an interface is formed between the water layer and the organic layer. The HMPs on the semiconductor nanoparticle surface by which the nanoparticle is stabilized in the water layer are substituted with TOP/TOPO at the interface, so that the semiconductor nanoparticle is now stabilized by TOP and/or TOPO and transported into the organic layer. Thereafter, the organic layer is extracted and purified to obtain the semiconductor nanoparticle stabilized by TOP and/or TOPO. Impurities that have not been reacted, such as Cd ions, S ions and hexametaphosphate, remain in the water layer and can therefore be mostly removed. The CdS semiconductor nanoparticle having TOP and/or TOPO as the stabilizer is then mixed with zinc oxide, 1-tetradecane phosphoric acid (TDPA), tri-n-octyl phosphine oxide (TOPO), tri-n-octyl phosphine (TOP), and S (powder) and then reacted under a high-temperature environment. As a result, the CdS semiconductor nanoparticle surface is coated with a ZnS inorganic component, and the energy band that existed in the forbidden band in the semiconductor nanoparticle is eliminated.

EXAMPLES

The invention will be hereafter described by way of examples.

Preparation of a Semiconductor Nanoparticle

The present example employs one of a variety of methods for preparing semiconductor nanoparticles.

In a semiconductor nanoparticle, the proportion of its surface area to its volume is very large. As a result, semiconductor nanoparticles tend to coalesce very easily. In order to allow the semiconductor nanoparticles to exist stably, measures have to be taken to prevent them from colliding or fusing with each other. A variety of measures have been devised so far, which can be roughly divided into two types. One is the physical isolation of the semiconductor nanoparticles by placing them in a solid matrix and a polymer matrix. The other is the inactivation of the particle surface by chemically modifying the metal-ion site on the particle surface with a low-molecule organic matter having a high level of ability to form a complex with the metal-ion site.

Based on the latter concept, the present example employed hexametaphosphate as the stabilizer. One thousand ml of an aqueous solution of sodium hexametaphosphate (0.1 mmol) and cadmium perchlorate Hexahydrate (0.2 mmol) was prepared and adjusted to pH 10.3. Nitrogen gas was bubbled into the solution, and then hydrogen sulfide gas (0.2 mmol) was injected into the solution while stirring vigorously. Stirring was continued for a while thereafter, during which time the solution changed from optically transparent and colorless to optically transparent yellow.

At this point, semiconductor nanoparticles that have been stabilized by hexametaphosphate already exist in the solution, but these semiconductor nanoparticles have a wide grain-size distribution, with their standard deviation exceeding 15% of the average grain size. As the physicochemical properties of a semiconductor nanoparticle depend on its grain size due to a quantum-size effect, the physical properties of these semiconductor nanoparticles in this state are averaged and their potential characteristics as semiconductor nanoparticles cannot be fully tapped. Thus, there is a need to chemically separate the semiconductor nanoparticles having a wide grain-size distribution immediately after preparation into individual grain sizes accurately and extract only those semiconductor nanoparticles of a specific grain size in order to attain a monodisperse distribution. In the present example, a size-selective photocorrosion was employed.

Achieving a Monodisperse Distribution of the Semiconductor Nanoparticles with a Size-Selective Photocorrosion The size-selective photocorrosion takes advantage of the fact that as the grain size of a semiconductor nanoparticle decreases, its energy gap increases due to a quantum-size effect, and that a metal chalcogenide semiconductor is oxidatively dissolved when irradiated by light in the presence of dissolved oxygen. Thus, the method irradiates the semiconductor nanoparticles having a wide grain-size distribution with monochromatic light of a shorter wavelength than the wavelength of the semiconductor nanoparticle's absorption edge. This causes only the semiconductor nanoparticles of larger diameters to be selectively optically excited and dissolved, thus sorting the semiconductor nanoparticles into smaller grain sizes.

Nitrogen gas was bubbled into a solution of the semiconductor nanoparticles having a wide grain-size distribution, and then bubbling with oxygen was carried out for 10 min. Methylviologen was added into the solution to a concentration of 50 $\mu$mol/l, and the solution was irradiated with a laser beam under stirring. The wavelength of the laser beam was shifted to the shorter-wavelength side in a stepwise manner. The light source included a 600-mV argon ion laser (Model 5500AMC-00 from Ion Laser Technology), a 500 WHg lamp (Model UI-501C from Ushio Inc) and an optical filter (Color glass filters L-39 and Y-43 from Toshiba) which were used selectively depending on the wavelength required.

When irradiated with light of wavelength 476.5 nm, the resultant semiconductor nanoparticles had an average grain size of 3.2 nm and a standard deviation of 0.19 nm, thus exhibiting a very narrow grain-size distribution where the standard deviation is about 6% of the average grain size. Thus, a solution of semiconductor nanoparticles with a close-to-monodisperse distribution was obtained.

Extraction of Semiconductor Nanoparticles

For a reason that will be explained later, it is desirable to coat the semiconductor nanoparticle with an organic and an inorganic component. A method of coating a semiconductor nanoparticle with ZnS in a nonpolar solvent is established. This method requires the semiconductor nanoparticle to be stabilized by TOP and/or TOPO, for example. Therefore, in order to coat the semiconductor nanoparticles stabilized by hexametaphosphate with ZnS by using the above method, the semiconductor nanoparticles have to be transformed into semiconductor nanoparticles stabilized by TOP and/or TOPO.

Hereafter, a method will be described that will extract the semiconductor nanoparticles while at the same time substituting the stabilizer, namely hexametaphosphate, on the surface of the semiconductor nanoparticles with TOP and/or TOPO. In this extraction method, the stabilizer on the semiconductor nanoparticle surface is substituted and at the same time extraction is carried out. Specifically, the surface of the semiconductor nanoparticles that have been stabilized by hexametaphosphate, which is stable in an aqueous layer, is made lipophilic by substitution with TOP and/or TOPO, and the organic layer, into which the semiconductor nanoparticles stabilized by TOP and/or TOPO have been transported, is extracted to recover the nanoparticles.

The 1000 ml hexametaphosphate semiconductor nanoparticle solution obtained by the above-described size-selective photocorrosion was condensed to 150 ml by evaporation. Ten or four grams of TOP, and seven or 10 grams of TOPO were added, and the solution was stirred for a long time. In this case, the ratios and the total amount of TOP and/or TOPO are not particularly limited. Thereafter, 100 ml of hexane was added, and the organic layer was drawn off. After adding anhydrous sodium sulfate, the recovered solution was stirred and subjected to ultrafiltration under reduced pressure. The filtrate was then evaporated to remove hexane. The resultant solution was added to anhydrous methanol, and the precipitate was recovered by centrifugation (5000 rpm, 10 min). After washing with anhydrous butanol, the recovery of the precipitate by centrifugation (5000 rpm, 10 min) was repeated several times, thereby obtaining semiconductor nanoparticles stabilized by TOP and/or TOPO.

Preparation of the Multi-Layer Semiconductor Nanoparticle

The semiconductor nanoparticles extracted by the above-described extraction method are identical to the semiconductor nanoparticles obtained by the size-selective photocorrosion. Thus, they have a very narrow grain-size distribution and already possess the characteristics required of semiconductor nanoparticles. However, the semiconductor nanoparticles in this state have the energy level of the semiconductor nanoparticle surface in the forbidden band, so that a good light-emission characteristic cannot be obtained. Therefore, it is desirable to coat the bulk semiconductor nanoparticle with an organic and an inorganic component in order to remove the energy level existing in the forbidden band.

Various ways of coating the bulk semiconductor nanoparticle have been attempted in the art. Examples include coating CdSe with tri-n-octyl phosphine (TOP) and tri-n-octyl phosphine oxide (TOPO), CdSe with CdS, CdS with ZnS, Si with $SiO_2$, CdSe with ZnS, and ZnS with CdSe. In the present example, a method of coating a CdS semiconductor nanoparticle stabilized by TOP and/or TOPO with ZnS will be described.

The semiconductor nanoparticles stabilized by TOP and/ or TOPO as described above were mixed in a reaction vessel with zinc oxide (2.5 mmol), TDPA (5 mmol), and TOPO (7.7 g) in the presence of nitrogen gas. The powder was then heated to 300° C. in the reaction vessel to obtain an optically transparent yellow solution. The solution was then stirred and cooled to 270° C., when S (powder) (1 mmol) and TOP (4 g) were slowly injected. Thereafter, the temperature was lowered to 150° C. and reaction was continued for six hours.

Then, the full volume of the reacted solution was drained by a syringe and rapidly injected into 25 ml of anhydrous methanol where it was quenched. After centrifugation (5000 rpm, 10 min), the precipitate was recovered from the solution. The precipitate was washed with an anhydrous butanol solution and then centrifuged (5000 rpm, 10 min) to recover the precipitate. This process of recovering the precipitate was repeated several times. The precipitate was eventually dissolved in hexane, and the solution was centrifuged (5000 rpm, 10 min) to recover the supernatant. The supernatant was evaporated to prepare powdered multi-layer semiconductor nanoparticles.

Figure 2:
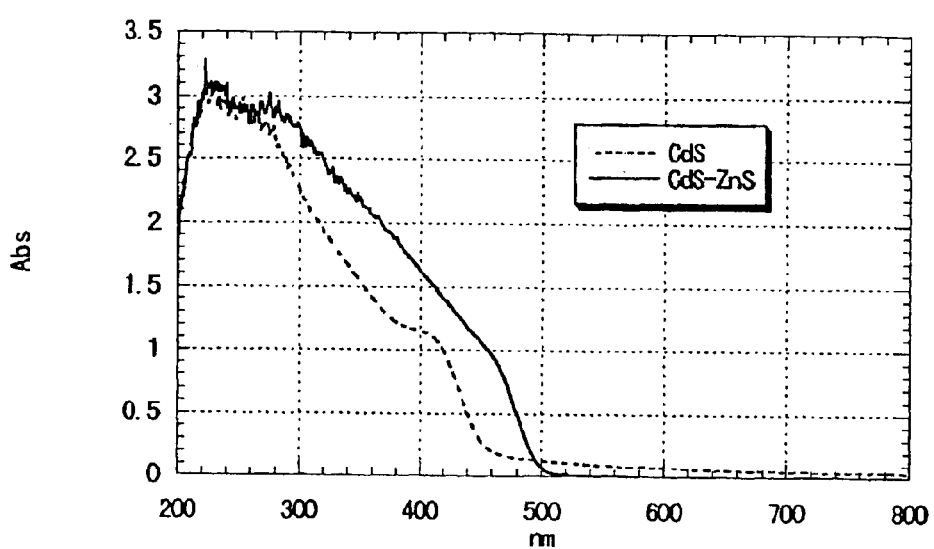
FIG. 2 shows the absorption spectrum of a multi-layer semiconductor nanoparticle in which CdS is coated with ZnS, and the absorption spectrum of a semiconductor nanoparticle made up only of CdS.
Figure 3:
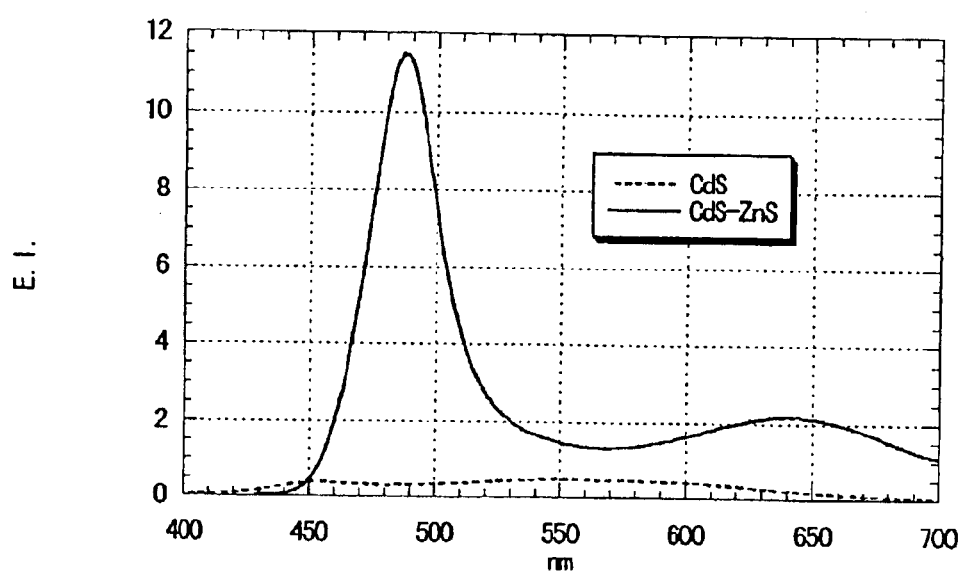
FIG. 3 shows the fluorescence spectrum of a multi-layer semiconductor nanoparticle obtained by coating CdS with ZnS, and the fluorescence spectrum of a semiconductor nanoparticle made up only of CdS.

FIG. 2 shows the absorption spectrum of the multi-layer semiconductor nanoparticles obtained by coating the thus manufactured CdS with ZnS, and the absorption spectrum of semiconductor nanoparticles made up only of CdS for comparison. FIG. 3 shows the fluorescence spectrum of the multi-layer semiconductor nanoparticles obtained by coating the CdS with ZnS, and the fluorescence spectrum of semiconductor nanoparticles made up only of CdS for comparison.

As described above, in accordance with the semiconductor nanoparticle manufacturing method utilizing the size-selective photocorrosion technique, large quantities of semiconductor nanoparticles having a very narrow grain-size distribution can be manufactured very easily. Further by coating the surface of semiconductor nanoparticles with an inorganic component in order to remove the energy band in the forbidden band, multi-layer semiconductor nanoparticles that exhibit a spectrum having a narrow wavelength-width peak can be prepared. However, heretofore it was difficult to combine these two techniques because of the problem arising from the difference in the stabilizer used. This problem has been solved by the present invention, which makes it possible to prepare multi-layer nanoparticles having the advantages of both of the techniques. The invention has also made it possible to use such stable materials as zinc oxide, 1-tetradecane phosphoric acid (TDPA), tri-n-octyl phosphine oxide (TOPO), tri-n-octyl phosphine (TOP), and S (powder) in achieving the multi-layer structure.

The multi-layer semiconductor nanoparticles manufactured according to the present invention exhibit a spectrum having a narrow wavelength-width peak. Therefore, when used for the detection of biopolymers, the multi-layer semiconductor nanoparticles allow a great deal of information to be detected easily. The semiconductor nanoparticles according to the invention are also potentially applicable to bio-imaging.

What is claimed is:

1. A method of manufacturing a multi-layer semiconductor nanoparticle, which comprises the steps of:
    transforming the nature of a solution of monodisperse semiconductor nanoparticles stabilized by a surface stabilizer between a hydrophilic and a lipophilic solution by substituting the surface stabilizer;
    transporting the stabilized semiconductor nanoparticles between an aqueous layer and an organic layer;
    coating the semiconductor nanoparticles in the layer to which the stabilized semiconductor nanoparticles have been transported with multiple layers; and
    separating the layer to which the stabilized semiconductor nanoparticles have been transported to recover the semiconductor nanoparticles therefrom.

2. The method of manufacturing a multi-layer semiconductor nanoparticle according to claim 1, wherein the monodisperse semiconductor nanoparticles are obtained by a size-selective photocorrosion.

3. The method of manufacturing a multi-layer semiconductor nanoparticle according to claim 1, wherein the monodisperse semiconductor nanoparticles are obtained by a reversed micelle method.

4. The method of manufacturing a multi-layer semiconductor nanoparticle according to claim 1, wherein the surface stabilizer for providing the hydrophilicity is hexametaphosphate, polyvinyl pyrrolidone, glycol dimethyl ether, or a thiol compound.

5. The method of manufacturing a multi-layer semiconductor nanoparticle according to claim 1, wherein the surface stabilizer for providing the lipophilicity is at least one selected from the group consisting of tri-n-octyl phosphine and tri-n-octyl phosphine oxide.

6. The method of manufacturing a multi-layer semiconductor nanoparticle according to claim 1, wherein semiconductor nanoparticles whose nature has been transformed from hydrophilic to lipophilic are reacted with zinc oxide, 1-tetradecane phosphoric acid (TDPA), tri-n-octyl phosphine oxide (TOPO), tri-n-octyl phosphine (TOP), and S (powder) in a high-temperature environment.

7. The method of manufacturing a multi-layer semiconductor nanoparticle according to claim 1, wherein the material of the core and the material of the layers uniformly coated on the surface of the core is ZnO, ZnS, ZnSe, ZnTe, CdO, CdS, CdSe, CdTe, HgS, HgSe, HgTe, InP, InAs, GaN, GaP, GaAs, $TiO_2$, $WO_3$, PbS or PbSe.

8. The method of manufacturing a multi-layer semiconductor nanoparticle according to claim 7, wherein the material of the core is CdS, and the material of the layers uniformly coated on the surface of the core is ZnS.

9. The multi-layer semiconductor nanoparticle manufactured by the method according to claim 1, which, when excited, emits fluorescence having a peak in a narrow wavelength-width region with a full width at half maximum (FWHM) of about 50 nm or less.

10. The multi-layer semiconductor nanoparticle manufactured by the method according to claim 9, wherein the nanoparticle exhibits less than 10% rms deviation in the diameter of the core.

* * * * *